(12) United States Patent
Nandi et al.

(10) Patent No.: US 10,308,611 B2
(45) Date of Patent: Jun. 4, 2019

(54) PROCESS FOR THE PREPARATION OF LORCASERIN HYDROCHLORIDE

(71) Applicant: AUROBINDO PHARMA LTD, Telangana, Hyderabad (IN)

(72) Inventors: Sukumar Nandi, Hyderabad (IN); Akkina Naresh, Hyderabad (IN); Syam Prasad Reddy Rao Annareddy, Hyderabad (IN); Gona Bala Narsimha Reddy, Hyderabad (IN); Meenakshi Sunderam Sivakumaran, Hyderabad (IN)

(73) Assignee: Aurobindo Pharma Ltd, Hyderabad (IN)

( * ) Notice: Subject to any disclaimer, the term of this patent is extended or adjusted under 35 U.S.C. 154(b) by 0 days.

(21) Appl. No.: 15/741,722

(22) PCT Filed: Mar. 18, 2016

(86) PCT No.: PCT/IB2016/051535
§ 371 (c)(1),
(2) Date: Jan. 3, 2018

(87) PCT Pub. No.: WO2016/151451
PCT Pub. Date: Sep. 29, 2016

(65) Prior Publication Data
US 2018/0194734 A1 Jul. 12, 2018

(30) Foreign Application Priority Data
Mar. 24, 2015 (IN) ............. 1487/CHE/2015

(51) Int. Cl.
*C07D 223/16* (2006.01)
(52) U.S. Cl.
CPC ........ *C07D 223/16* (2013.01); *C07B 2200/13* (2013.01)

(58) Field of Classification Search
CPC .................................................. C07D 223/16
USPC .......................................................... 540/576
See application file for complete search history.

(56) References Cited

FOREIGN PATENT DOCUMENTS

WO    WO2012030927    *    3/2012    ............... A61K 9/20

OTHER PUBLICATIONS https://pubs.acs.org/doi/abs/10.1021/op4002565; last accessed Sep. 26, 2018.*
http://www.rsc.org/suppdata/gc/c0/c0gc00918k/c0gc00918k.pdf; last accessed Sep. 26, 2018.*
http://www.chem.utoronto.ca/coursenotes/CHM249/Recrystallization. pdf, last accessed, Sep. 28, 2018.*

* cited by examiner

*Primary Examiner* — Jeffrey H Murray
(74) *Attorney, Agent, or Firm* — Jay R. Akhave

(57) ABSTRACT

The present invention provides a process for the preparation of crystalline Lorcaserin hydrochloride hemihydrate of Formula (Ia), which comprises, Formula (Ia) (i) providing a solution of Lorcaserin base in a solvent; (ii) if water is present, removing water from the reaction mixture; (iii) adding hydrogen chloride to the reaction mixture; (iv) combining the reaction mixture with a suitable anti-solvent; and (v) isolating the crystalline Lorcaserin hydrochloride hemihydrate of Formula (Ia).

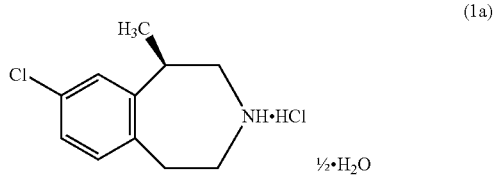

(Ia)

8 Claims, No Drawings

PROCESS FOR THE PREPARATION OF LORCASERIN HYDROCHLORIDE

FIELD OF THE INVENTION

The present invention relates to a process for the preparation of Lorcaserin hydrochloride hemihydrate of Formula Ia.

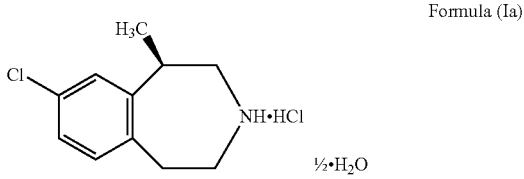

Formula (Ia)

BACKGROUND OF THE INVENTION

Lorcaserin of Formula (I) is chemically known as (R)-8-chloro1-methyl-2,3,4,5-tetrahydro-1H-3-benzazepine hydrochloride. Lorcaserin hydrochloride of Formula (I) is an agonist of the 5-$HT_{2C}$ receptor and shows effectiveness at reducing obesity in animal models and humans. Further, 5-$HT_{2C}$ receptor is recognized as a well-accepted receptor target for the treatment of obesity, psychiatric, and other disorders. Lorcaserin hydrochloride of Formula (I) is approved as anti-obesity agent and is marketed under the brand name Belviq in USA.

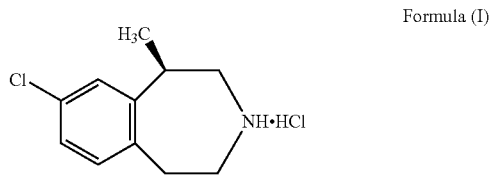

Formula (I)

U.S. Pat. No. 6,953,787 discloses Lorcaserin or a pharmaceutically acceptable salt, solvate or hydrate thereof. US '787 also discloses the process for the preparation of Lorcaserin or a pharmaceutically acceptable salt comprising the step of deprotecting N-trifluoroacetyl-8-chloro-1-methyl-2,3,4,5-tetrahydro-1H-3-benzazepine or a pharmaceutically acceptable salt to form Lorcaserin or a pharmaceutically acceptable salt.

U.S. Pat. No. 8,168,624 disclose crystalline forms of Lorcaserin hydrochloride, namely three crystalline forms of Lorcaserin hydrochloride, individually designated as Form I, Form II and Form III (hemihydrate) of Lorcaserin hydrochloride. Form I and Form II of Lorcaserin hydrochloride are anhydrous, hygroscopic forms, both of which readily convert to Form III (hemihydrate) of Lorcaserin hydrochloride of Formula (Ia), upon exposure to moisture.

US '624 also discloses a process for the preparation of Lorcaserin hydrochloride hemihydrate of Formula (Ia) which comprises mixing Lorcaserin hydrochloride of Formula (I) with a crystallizing solvent containing water and inducing precipitation of the Lorcaserin hydrochloride hemihydrate of Formula (Ia) from the crystallizing solvent.

The process is shown in Scheme-I as given below:

Scheme I

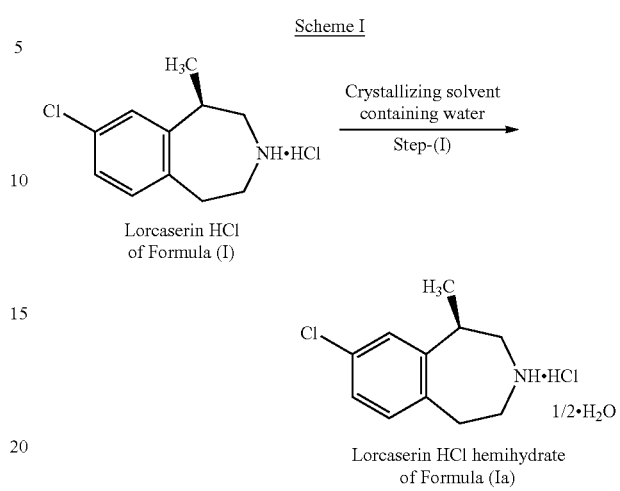

US 2013/0158013 discloses a crystalline Form IV of Lorcaserin hydrochloride, is an anhydrous polymorph. Further US '013 disclose that Lorcaserin hydrochloride crystalline Form IV is the most stable of anhydrous polymorphs at ambient temperature.

US '013 also disclose a process for the preparation of Lorcaserin hydrochloride hemihydrate (Form III), comprising slurrying a first mixture comprising Lorcaserin hydrochloride salt Form IV and a first solvent to form (R)-Lorcaserin HCl hemihydrate (Form III).

However, the above processes suffer from low yield and low purity of Lorcaserin HCl hemihydrate (Form III). Therefore, these processes of making Lorcaserin HCl hemihydrate (Form III) are not commercially feasible.

However, there is always a need for an alternative process, which for example, involves use of reagents/solvents that are less expensive and easier to handle, consume smaller amounts of solvents, and provide a higher yield of product with higher purity.

Hence, there is a need to develop cost effective and commercially viable process for the preparation of Lorcaserin hydrochloride of Formula (I).

The present invention directed towards a process for the preparation of crystalline Lorcaserin hydrochloride hemihydrate of Formula (Ia) with high purity and high yield.

Objective of Invention

The main objective of the present invention is to provide a simple and cost-effective process for the preparation of crystalline Lorcaserin hydrochloride hemihydrate of Formula (Ia) with high purity and good yield on commercial scale.

SUMMARY OF THE INVENTION

The present invention provides a process for the preparation of crystalline Lorcaserin hydrochloride hemihydrate of Formula (Ia), which comprises,

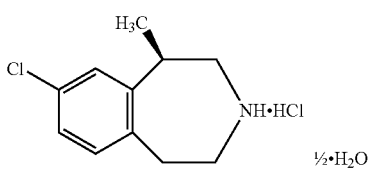

Formula (Ia)

(i) providing a solution of Lorcaserin base in a solvent;
(ii) if water is present, removing water from the reaction mixture;
(iii) adding hydrogen chloride to the reaction mixture;
(iv) combining the reaction mixture with a suitable anti-solvent; and
(v) isolating the crystalline Lorcaserin hydrochloride hemihydrate of Formula (Ia).

DETAILED DESCRIPTION OF THE INVENTION

In one embodiment of the present invention provides a process for the preparation of crystalline Lorcaserin hydrochloride hemihydrate of Formula (Ia), which comprises,

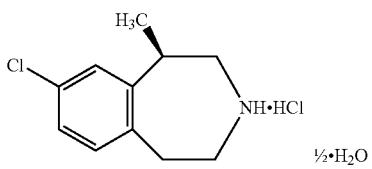

Formula (Ia)

(i) providing a solution of Lorcaserin base in a solvent;
(ii) if water is present, removing water from the reaction mixture;
(iii) adding hydrogen chloride to the reaction mixture;
(iv) combining the reaction mixture with a suitable anti-solvent; and
(v) isolating the crystalline Lorcaserin hydrochloride hemihydrate of Formula (Ia).

In another embodiment of the present invention, solvent used in step-(i) comprises from ester, halogenated hydrocarbon, ketone, aromatic hydrocarbon or mixture thereof.

In another embodiment of the present invention, ester comprises from ethyl acetate, n-propyl acetate, n-butyl acetate, isobutyl acetate, t-butyl acetate, methyl acetate or mixtures thereof; halogenated hydrocarbon comprises from dichloromethane, 1,2-dichloroethane, chloroform, carbon tetrachloride, or mixtures thereof; ketone comprises from acetone, ethyl methyl ketone, diethyl ketone, methyl isobutyl ketone, methyl-pentane-2-one or mixtures thereof; aromatic hydrocarbon comprises from toluene, m-xylene, o-xylene, p-xylene or mixtures thereof.

Yet another embodiment of the present invention, the process of removing water in step-(ii) from the reaction mixture preferably comprises azeotropic distillation.

In some embodiment of the present invention, in step-(iii) hydrogen chloride gas is passed into the reaction mass or hydrogen chloride in an anhydrous solvent comprises ester or alcohol or mixtures thereof is added to the reaction mass to produce Lorcaserin hydrochloride (I).

In some embodiment of the present invention, ester comprises from ethyl acetate, n-propyl acetate, n-butyl acetate, isobutyl acetate, t-butyl acetate, methyl acetate or mixtures thereof; alcohol comprises from methanol, ethanol, ethylene glycol, 1-propanol, 2-propanol (isopropyl alcohol), 2-methoxyethanol, 1-butanol, 2-butanol or mixtures thereof.

In another embodiment of the present invention, anti-solvent used in step-(iv) comprises from cyclohexane, pentane, hexane, toluene, cycloheptane, methyl cyclohexane, heptane, or mixture thereof.

In some embodiments, the mixture containing the crystallizing solvent and Lorcaserin hydrochloride is maintained at a temperature of about 40 to about 80, about 50 to about 70, or about 60° C. prior to inducing precipitation for a period of about 1 to 24 hours.

In some embodiments, Lorcaserin hydrochloride is dissolved in the crystallizing solvent prior to inducing precipitation. The dissolution can be achieved by heating the mixture to a suitable temperature such as between about 40 and about 80° C.

In some embodiments, precipitation of the Lorcaserin hydrochloride hemihydrate product can be induced by adding anti solvent.

In some embodiments, the mixture is cooled to a temperature of about −15 to about 15° C.

In some embodiments, the mixture is cooled to a temperature of about −5 to about 10° C.

In further embodiments, the mixture is cooled to a temperature of about 0 to about 5° C.

In another embodiment of the present invention, crystalline Lorcaserin hydrochloride hemihydrate of Formula (Ia) is isolated by conventional techniques such as filtration and dried the product.

In some embodiment of the present invention, the present invention provides a compound which is Lorcaserin hydrochloride hemihydrate (Ia) gains less than about 1.0%, less than about 0.5% or less than about 0.2% weight after undergoing a dynamic vapor sorption cycle.

In some embodiment of the present invention, Lorcaserin hydrochloride hemihydrate (Form III) shows that it is substantially non-hygroscopic, adsorbing less than 0.5 wt % water at 90% RH and the XRPD pattern showed no change in crystalline form after the dynamic vapor sorption.

In some embodiment of the present invention, Lorcaserin base which is used as starting material in the present invention can be prepared for example by the procedure disclosed in U.S. Pat. No. 8,367,657.

The process disclosed in US '657 involves chlorination of 4-Chlorophenylethyl alcohol to produce 4-Chlorophenylethyl chloride, followed by condensed with 1-aminopropan-2-ol to produce 1-[(4-chlorophenethyl)amino]propan-2-ol, which is further treated with chlorinating agent to produce 2-Chloro-N-(4-chlorophenethyl)-propan-1-amine. The compound 2-Chloro-N-(4-chlorophenethyl)-propan-1-amine undergoes cyclisation to produce Racemic Lorcaserin, followed by resolution to produce Lorcaserin Base.

The following examples illustrate the nature of the invention and are provided for illustrative purposes only and should not be construed to limit the scope of the invention.

EXAMPLES

Example-1

Process for the Preparation of Crystalline Lorcaserin Hydrochloride Hemihydrate Lorcaserin hemitartrate monohydrate salt (100 g) was suspended in ethyl acetate (300 mL) and DM water (300 mL) at 20-30° C. The above suspension was cooled to 10-15° C. 40%. w/w Sodium hydroxide solution (38.13 g) was slowly added for about 30 mins to the reaction mixture at 10-15° C. and stirred for 30 minutes. The reaction mass temperature was raised to 20-25° C. Organic layer was separated and the aqueous layer was extracted with ethyl acetate (200 mL). Combined the organic layer and the organic layer was washed with 20% aqueous sodium chloride (400 mL). The solvent from the organic layer was evaporated under reduced pressure at below 40° C. to afford oily material. The oily material is dissolved in ethyl acetate (100 mL) at 20-30° C. The reaction mass was cooled to 0-5° C. Ethyl acetate-hydrogen chloride (15% w/w, 101.21 g) was slowly added for about 30 mins to the reaction mixture at 0-5° C. n-heptane (400 mL) was slowly added for about 30 mins at 0-5° C. and stirred for 3 hours at same temperature. The reaction mass was filtered and washed with pre-cooled n-heptane (100 mL). The obtained solid was dried at 30-40° C. under reduced pressure to afford 75 g of the title compound.

Yield: 90% of theory;
Purity: 99.93%

Example-2

Process for the Preparation of Crystalline Lorcaserin Hydrochloride Hemihydrate

Lorcaserin hemitartrate monohydrate salt (100 g) was suspended in ethyl acetate (200 mL) and DM water (200 mL) at 20-30° C. The above suspension was cooled to 10-15° C. 40% w/w Sodium hydroxide solution (38.13 g) was slowly added for about 30 mins to the reaction mixture at 10-15° C. and stirred for 30 minutes. The reaction mass temperature was raised to 20-25° C. Organic layer was separated and the aqueous layer was extracted with ethyl acetate (200 mL). Combined the organic layer and the organic layer was washed with 20% aqueous sodium chloride (400 mL). The solvent from the organic layer was evaporated under reduced pressure at below 40° C. to afford oily material. The oily material is dissolved in ethyl acetate (200 mL) at 20-30° C. The reaction mass was cooled to 0-5° C. Ethyl acetate-hydrogen chloride (15% w/w, 101.21 g) was slowly added for about 30 mins to the reaction mixture at 0-5° C. n-heptane (600 mL) was slowly added for about 30 mins at 0-5° C. and stirred for 3 hours at same temperature. The reaction mass was filtered and washed with pre-cooled n-heptane (100 mL). The obtained solid was dried at 30-40° C. under reduced pressure to afford 76 g of the title compound.

Yield: 90% of theory;
Purity: 99.95%

We claim:
1. A process for the preparation of crystalline Lorcaserin hydrochloride hemihydrate of Formula (Ia), which comprises,

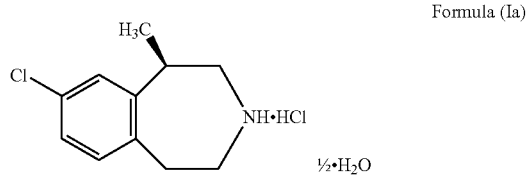

Formula (Ia)

(i) providing a solution of Lorcaserin base in a solvent;
(ii) adding hydrogen chloride to the reaction mixture;
(iii) combining the reaction mixture with a suitable anti-solvent; and
(iv) isolating the crystalline Lorcaserin hydrochloride hemihydrate of Formula (Ia).

2. The process as claimed in claim 1, wherein the solvent used in step (i) is selected from the group comprising an ester, a halogenated hydrocarbon, a ketone, an aromatic hydrocarbon or a mixture thereof.

3. The process according to claim 2, wherein the ester comprises ethyl acetate, n-propyl acetate, n-butyl acetate, isobutyl acetate, t-butyl acetate, methyl acetate; the halogenated hydrocarbon comprises dichloromethane, 1,2-dichloroethane, chloroform, carbon tetrachloride; the ketone comprises acetone, ethyl methyl ketone, diethyl ketone, methyl isobutyl ketone, methyl-pentane-2-one; and the aromatic hydrocarbon comprises toluene, m-xylene, o-xylene, p-xylene or mixtures thereof.

4. The process as claimed in claim 1, wherein step (ii) is carried out in the presence of a solvent selected from the group comprising an ester, an alcohol or a mixtures thereof.

5. The process as claimed in claim 4, wherein the ester is selected from the group comprising ethyl acetate, n-propyl acetate, n-butyl acetate, isobutyl acetate, t-butyl acetate, methyl acetate or mixtures thereof.

6. The process as claimed in claim 4, wherein the alcohol is selected from the group comprising methanol, ethanol, ethylene glycol, 1-propanol, 2-propanol (isopropyl alcohol), 2-methoxyethanol, 1-butanol, 2-butanol or mixtures thereof.

7. The process as claimed in claim 1, wherein the anti-solvent used in step (iii) comprises cyclohexane, pentane, hexane, toluene, cycloheptane, methyl cyclohexane, heptane or mixtures thereof.

8. The process as claimed in claim 1, wherein isolation of crystalline Lorcaserin hydrochloride hemihydrate of Formula (Ia) is performed by filtration and drying.

* * * * *